(12) United States Patent
Itoh et al.

(10) Patent No.: US 10,401,287 B2
(45) Date of Patent: Sep. 3, 2019

(54) LIGHTING DEVICE, AND APPARATUS AND SYSTEM INCORPORATING THE LIGHTING DEVICE

(71) Applicants: Hitoshi Itoh, Kanagawa (JP); Fumihiro Nakashige, Kanagawa (JP); Kenji Kobayashi, Kanagawa (JP)

(72) Inventors: Hitoshi Itoh, Kanagawa (JP); Fumihiro Nakashige, Kanagawa (JP); Kenji Kobayashi, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/880,989

(22) Filed: Jan. 26, 2018

(65) Prior Publication Data

US 2018/0209904 A1 Jul. 26, 2018

(30) Foreign Application Priority Data

Jan. 26, 2017 (JP) ................................ 2017-012007
Jan. 26, 2018 (JP) ................................ 2018-011191

(51) Int. Cl.
*G01N 21/57* (2006.01)
*G03G 15/00* (2006.01)
*G01N 21/55* (2014.01)

(52) U.S. Cl.
CPC ......... *G01N 21/57* (2013.01); *G03G 15/5062* (2013.01); *G01N 2021/556* (2013.01); *G01N 2201/0631* (2013.01); *G01N 2201/0642* (2013.01); *G01N 2201/06146* (2013.01); *G01N 2201/0813* (2013.01)

(58) Field of Classification Search
CPC ............. G01N 21/57; G01N 2021/556; G01N 2201/06146; G01N 2201/0631; G01N 2201/0642; G01N 2201/0813; G03G 15/5062; G01J 4/00; F21V 8/00
See application file for complete search history.

(56) References Cited

U.S. PATENT DOCUMENTS

| 5,576,825 | A | 11/1996 | Nakajima et al. |
| 6,031,620 | A | 2/2000 | Typpo |
| 6,079,854 | A | 6/2000 | Ra |
| 2007/0091309 | A1 | 4/2007 | Kondo |
| 2007/0229810 | A1 | 10/2007 | Kaya |

(Continued)

FOREIGN PATENT DOCUMENTS

| DE | 27 01 764 A1 | 7/1978 |
| EP | 1 843 145 A1 | 10/2007 |
| JP | 8-136252 | 5/1996 |

(Continued)

OTHER PUBLICATIONS

Extended European Search Report dated Apr. 17, 2018 in Patent Application No. 18153654.1, 5 pages.

*Primary Examiner* — Jamil Ahmed
(74) *Attorney, Agent, or Firm* — Oblon, McClelland, Maier & Neustadt, L.L.P.

(57) ABSTRACT

A lighting device includes: a light emitting device including a plurality of light emitting elements arranged in curve having a first curvature; and a honeycomb member having an extendable and contractible honeycomb structure, arranged in curve having a second curvature larger than the first curvature, in an emission direction of light emitted from the light emitting device.

8 Claims, 11 Drawing Sheets

(56) References Cited

U.S. PATENT DOCUMENTS

2011/0279668 A1    11/2011  Nakashige et al.
2015/0268166 A1    9/2015  Mäntylä

FOREIGN PATENT DOCUMENTS

| JP | 9-210653 | 8/1997 | | |
| JP | 2008-046103 | 2/2008 | | |
| JP | 2008-116761 | 5/2008 | | |
| JP | 2009-168653 A | 7/2009 | | |
| JP | 2009168653 A | * 7/2009 | ......... | G01N 21/8803 |
| JP | 2011-242379 | 12/2011 | | |
| WO | WO 98/49541 A1 | 11/1998 | | |
| WO | WO 2014/068188 A1 | 5/2014 | | |

* cited by examiner

LIGHTING DEVICE, AND APPARATUS AND SYSTEM INCORPORATING THE LIGHTING DEVICE

CROSS-REFERENCE TO RELATED APPLICATIONS

This patent application is based on and claims priority pursuant to 35 U.S.C. § 119(a) to Japanese Patent Application Nos. 2017-012007, filed on Jan. 26, 2017, and 2018-011191, filed on Jan. 26, 2018, in the Japan Patent Office, the entire disclosure of which is hereby incorporated by reference herein.

BACKGROUND

Technical Field

The present invention generally relates to a lighting device, and an apparatus and system incorporating the lighting device, and more specifically, relates to a lighting device, a reading device, an inspection apparatus, and an inspection system.

Description of the Related Art

The background lighting device includes a light emitting device that emits substantially parallel light, and a curved mirror that reflects the substantially parallel light so as to irradiate an object with that light. According to such a lighting device, all of regularly reflected light from an object enters a reduction optical system such as a charge coupled device (CCD), resulting in generation of an image with the light level of the regularly reflected light from the object. Such an image indicates glossiness of the object, and is used for inspecting gloss of the object or the like.

However, in the background lighting device, a design has been made on the premise that a surface of the object on which substantially parallel light is incident has a specific degree of flatness (usually a perfect plane). Therefore, in a case where a surface of the object is a non-perfect plane having waviness or inclination, regularly reflected light from the object does not sufficiently enter a target area.

SUMMARY

Example embodiments of the present invention include a lighting device, which includes: a light emitting device including a plurality of light emitting elements arranged in curve having a first curvature; and a honeycomb member having an extendable and contractible honeycomb structure, arranged in curve having a second curvature larger than the first curvature, in an emission direction of light emitted from the light emitting device.

Example embodiments of the present invention include a reading device, which includes: the lighting device to emit the light to an inspection object; and an image sensor to detect a light level of a regularly reflected light that is reflected from the inspection object, the light level to be used for inspecting gloss of the inspection object.

Example embodiments of the present invention include an inspection apparatus including the reading device; and a controller to control the reading device.

Example embodiments of the present invention include an image forming apparatus to form an image on a recording material; and the inspection apparatus, wherein the inspection object is the recorded material having the image formed thereon.

BRIEF DESCRIPTION OF THE SEVERAL VIEWS OF THE DRAWINGS

A more complete appreciation of the disclosure and many of the attendant advantages and features thereof can be readily obtained and understood from the following detailed description with reference to the accompanying drawings, wherein.

Figure 1:
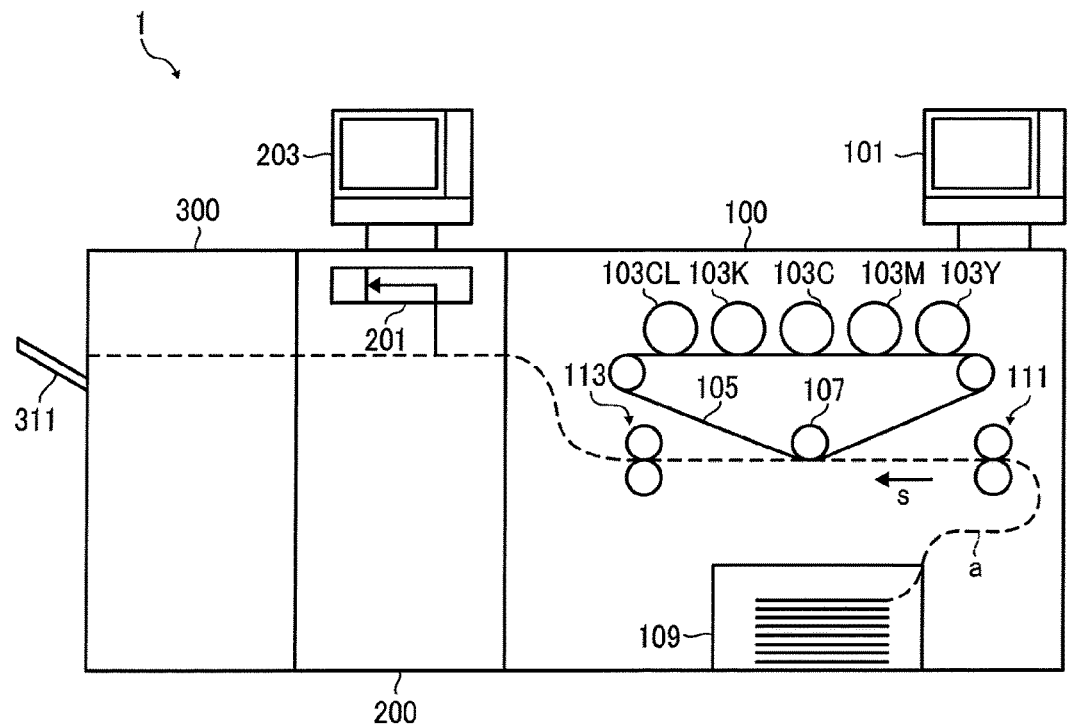
FIG. 1 is a schematic diagram illustrating a configuration of an inspection system according to an embodiment.

The accompanying drawings are intended to depict embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Hereinafter, a lighting device according to an embodiment of the present invention will be described in detail with reference to the accompanying drawings. In the following, the lighting device is used for inspecting gloss of a printed matter, however, application of the lighting device is not limited thereto.

FIG. 1 is a schematic diagram illustrating a configuration of an inspection system 1 according to the present embodiment. As illustrated in FIG. 1, the inspection system 1 includes an image forming apparatus 100, an inspection apparatus 200, and a stacker 300.

The image forming apparatus 100 includes a control panel 101, an image forming device including photoconductor drums 103Y, 103M, 103C, 103K, and 103CL, a transfer belt 105, a secondary transfer roller 107, a paper feeder 109, a conveying roller pair 111, a fixing device 113, and the like.

The control panel 101 functions as an operation unit for receiving various operation inputs from a user to the image forming apparatus 100. In addition, the control panel 101 functions as a display for displaying various screens to a user. The image forming device includes a charging device, an exposure unit, a developing device, a transfer unit, and a cleaning unit for removing a residual toner. The image forming device forms a toner image on a surface of each of the photoconductor drums 103Y, 103M, 103C, 103K, and 103CL by charging the surface of the photoconductor drum with the charging device, exposing light to the surface of the photoconductor drum with the exposure unit to form a latent image, and developing the latent image into a toner image with the developing device. The toner images formed on the photoconductor drums are sequentially transferred to the transfer belt 105 so as to be superimposed one above the other by the transfer unit. As a result, a full-color and glossy toner image is formed on the transfer belt 105. In the present embodiment, a yellow toner image is formed on the photoconductor drum 103Y, a magenta toner image is formed on the photoconductor drum 103M, a cyan toner image is formed on the photoconductor drum 103C, a black toner image is formed on the photoconductor drum 103K, and a clear toner image is formed on the photoconductor drum 103CL, but the present embodiment is not limited thereto.

The transfer belt 105 conveys the full-color toner image, which is generated by superimposing the toner images transferred from the photoconductor drums 103Y, 103M, 103C, 103K, and 103CL, to a secondary transfer position of the secondary transfer roller 107. In the present embodiment, first, a yellow toner image is transferred to the transfer belt 105, and subsequently, a magenta toner image, a cyan toner image, a black toner image, and a clear toner image are sequentially superimposed and transferred to the transfer belt 105, but the present embodiment is not limited thereto.

The paper feeder 109 stores a stack of recording sheets, and feeds the recording sheets one by one. As the recording sheet, any sheet, or material, capable of recording an image thereon, may be used, such as thermal paper, plain paper, roll paper, coated paper, cardboard, an overhead projector (OHP) sheet, a plastic film, a prepreg, or a copper foil. In the present embodiment, a case where the recording sheet is a cut sheet will be described as an example, but the present embodiment is not limited thereto.

The conveying roller pair 111 conveys the recording sheet fed by the paper feeder 109 in a direction of arrow s on a conveying path a.

The secondary transfer roller 107 collectively transfers the full-color toner image conveyed by the transfer belt 105 onto the recording sheet conveyed by the conveying roller pair 111 at the secondary transfer position.

The fixing device 113 fixes the full-color toner image to the recording sheet with heat and pressure.

The image forming apparatus 100 ejects the printed matter which is the recording sheet having the full-color toner image fixed thereon, to the inspection apparatus 200.

Figure 15:
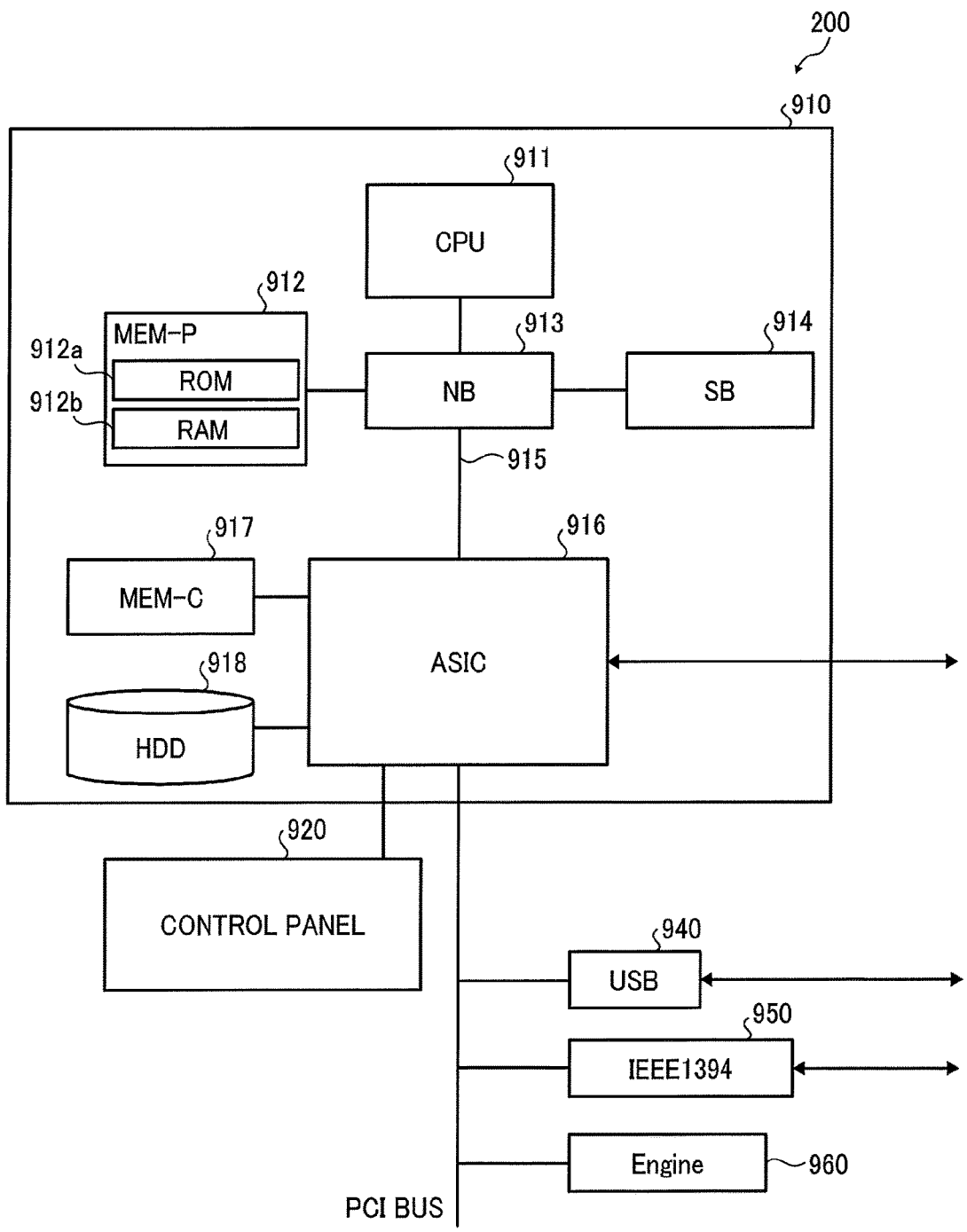
FIG. 15 is a block diagram illustrating an example of a hardware configuration of an inspection apparatus according to the present embodiment.

The inspection apparatus 200 includes a reader 201 and a control panel 203, and a controller 910 (see FIG. 15).

The control panel 203 functions as an operation unit for receiving various operation inputs from a user to the inspection apparatus 200. In addition, the control panel 203 functions as a display for displaying various screens. Note that the inspection apparatus 200 does not necessarily include the control panel 203. As an example, the control panel 101 may also serve as the control panel 203, or an externally coupled personal computer (PC) may also serve as the control panel 203.

Figure 2:
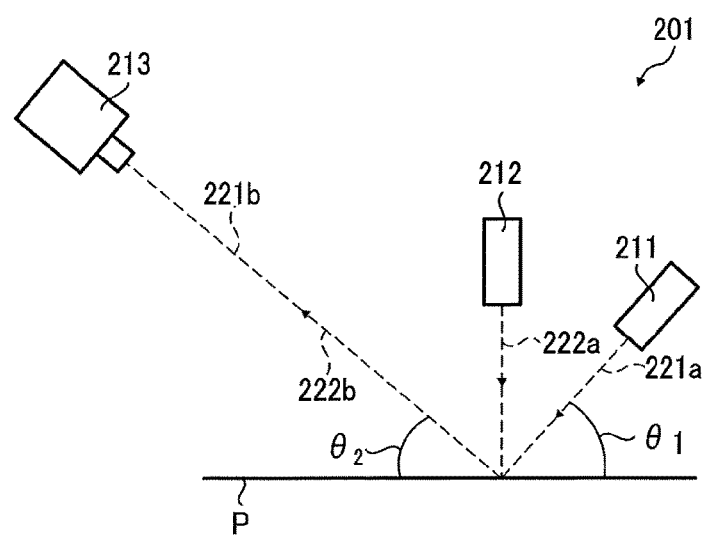
FIG. 2 is a schematic diagram illustrating an example of a reader n the inspection system of FIG. 1 according to the embodiment.

The reader 201 electrically reads the printed matter ejected from the image forming apparatus 100. FIG. 2 is a schematic diagram illustrating an example of the reader 201 according to the present embodiment. As illustrated in FIG. 2, the reader 201 includes a lighting device for gloss 211 (an example of a lighting device), a lighting device for concentration 212, and an image sensor 213.

The lighting device for gloss 211 irradiates a reading area (one line in a main scanning direction) of a printed matter P, which is a target for inspection, with illumination light $221a$ incident at a predetermined incident angle $\theta 1$. Regularly reflected light $221b$ is reflected light obtained by reflection of the illumination light $221a$, which is incident on the reading area of the printed matter P at the incident angle $\theta 1$ on the reading area, to the opposite side in the incident direction at a reflection angle $\theta 2$ ($\theta 2=\theta 1$). That is, regularly reflected light $221b$ is reflected light obtained by specular reflection of the illumination light $221a$ on the reading area. The details of the lighting device for gloss 211 will be described later.

The lighting device for concentration 212 irradiates a reading area of a printed matter P with illumination light $222a$ incident at a predetermined incident angle. The predetermined incident angle is any angle different from the incident angle $\theta 1$, and for example, 90 degrees. Diffusion reflection light $222b$ is reflected light obtained by reflection of the illumination light $222a$, which is incident on the reading area of the printed matter P at a predetermined incident angle on the reading area, at a reflection angle different from the predetermined incident angle (θ2 in the example illustrated in FIG. 2). That is, diffusion reflection light 222b is reflected light obtained by diffusion reflection of the illumination light 222a on the reading area. As the lighting device for concentration 212, for example, a diffusion lighting device such as a xenon lamp or an LED array may be used.

The image sensor 213 detects the light level of the regularly reflected light 221b, and the light level of the diffusion reflection light 222b. Therefore, the image sensor 213 is disposed at a position where the regularly reflected light 221b and the diffusion reflection light 222b can be received.

As the image sensor 213, for example, a reduction optical system in which a plurality of imaging elements is arranged in a direction (main scanning direction) parallel to the reading area of the printed matter P may be used. As the imaging element, for example, a metal oxide semiconductor device (MOS), a complementary metal oxide semiconductor device (CMOS), a charge coupled device (CCD), or a contact image sensor (CIS) may be used.

In the present embodiment, the lighting device for gloss 211 and the lighting device for concentration 212 do not simultaneously emit light, and alternately emit light in accordance with drive of the image sensor 213. In the present embodiment, each time the printed matter P is conveyed by one line in a sub-scanning direction, the lighting device for gloss 211 emits the illumination light 221a and the image sensor 213 reads the light level of the regularly reflected light 221b, and the lighting device for concentration 212 emits the Illumination light 222a and the image sensor 213 reads the light level of the diffusion reflection light 222b. The reader 201 repeats this operation while the printed matter P is conveyed by one line in the sub-scanning direction, until the entire reading area of the printer matter P is read. As a result, the reader 201 reads (generates) a glossiness image indicating glossiness of each pixel of the printed matter P having the light level of the regularly reflected light 221b, and a concentration image indicating a concentration of each pixel of the printed matter P having the light level of the diffusion reflection light 222b.

Glossiness is a numerical value indicating the degree of specular gloss, and is synonymous with specular glossiness specified by Japanese Industrial Standards (JIS) Z 8741 or International Organization for Standardization (ISO) 2813. That is, the glossiness image indicates a light level distribution of regularly reflected light in any observation direction as a gloss distribution of the printed matter P. The concentration image indicates a light level distribution of diffusion reflection light in any observation direction as a concentration distribution of the printed matter P.

Returning to FIG. 1, the inspection apparatus 200 ejects the printed matter on which reading has been completed to the stacker 300. Note that the inspection apparatus 200 may further include another reader for optically reading the other side of the printed matter. In this case, the reader for optically reading the other side of the printed matter has a similar configuration to the reader 201.

The stacker 300 includes a tray 311. The stacker 300 stacks the printed matter ejected by the inspection apparatus 200 on the tray 311.

Figure 3:
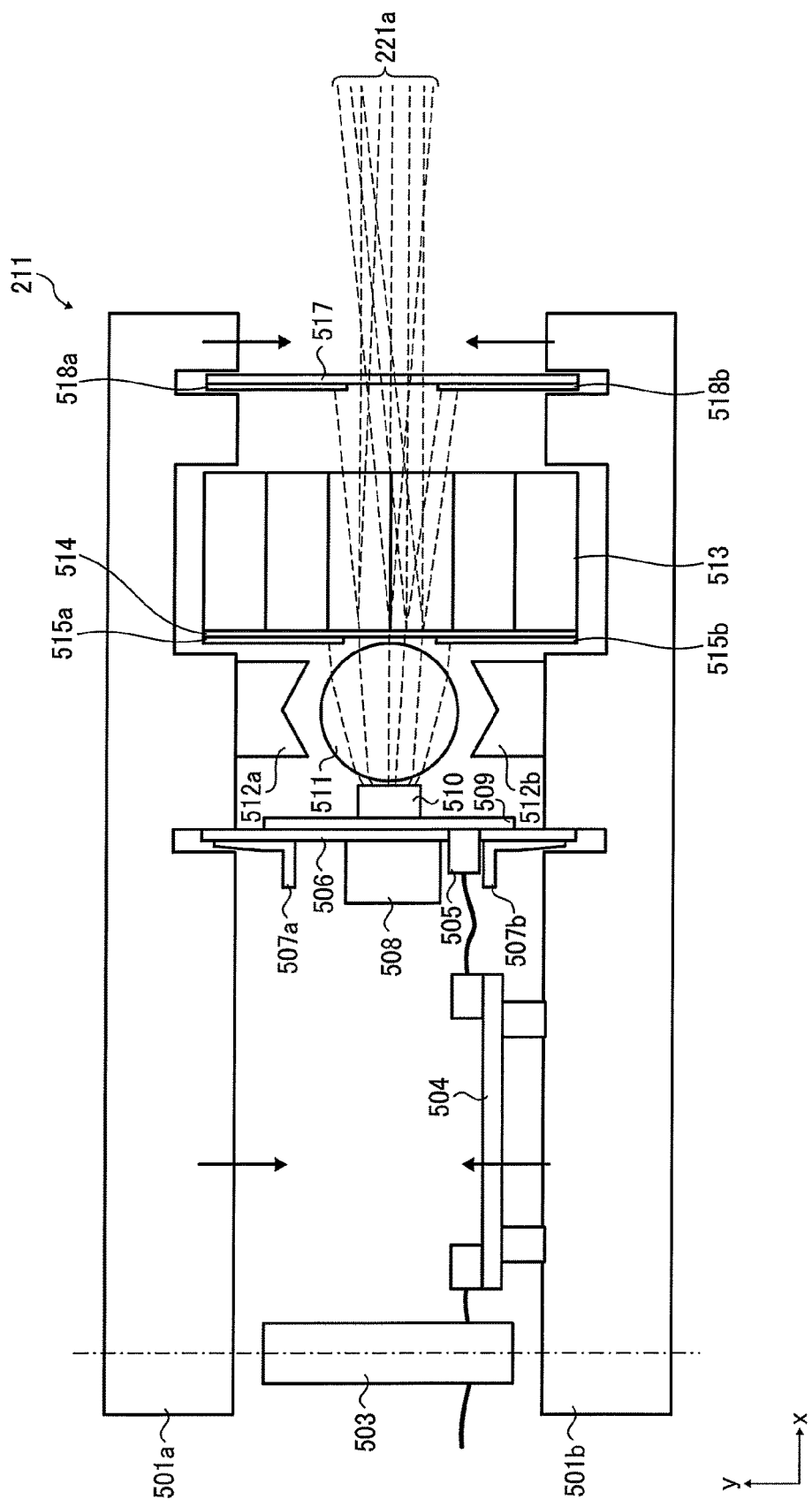
FIG. 3 is a side view illustrating a mechanical configuration of a lighting device for gloss according to the embodiment.

FIG. 3 is a diagram illustrating an example of a mechanical configuration of the lighting device for gloss 211 according to the present embodiment, and illustrates a side view seen through an internal structure of the lighting device for gloss 211. As illustrated in FIG. 3, the lighting device for gloss 211 includes bases 501a and 501b, a spacer 503, a power supply substrate 504, a connector 505, a base plate 506, shims 507a and 507b, a radiator 508, a flexible substrate 509, a light emitting diode array (LEDA) 510 (an example of a light emitting device), a rod lens 511, lens supports 512a and 512b, a honeycomb member 513, a diffusion transmission film 514, specular reflection films 515a and 515b, a dustproof film 517, and light shielding films 518a and 518b (an example of one or more light shielding members).

Figure 4:
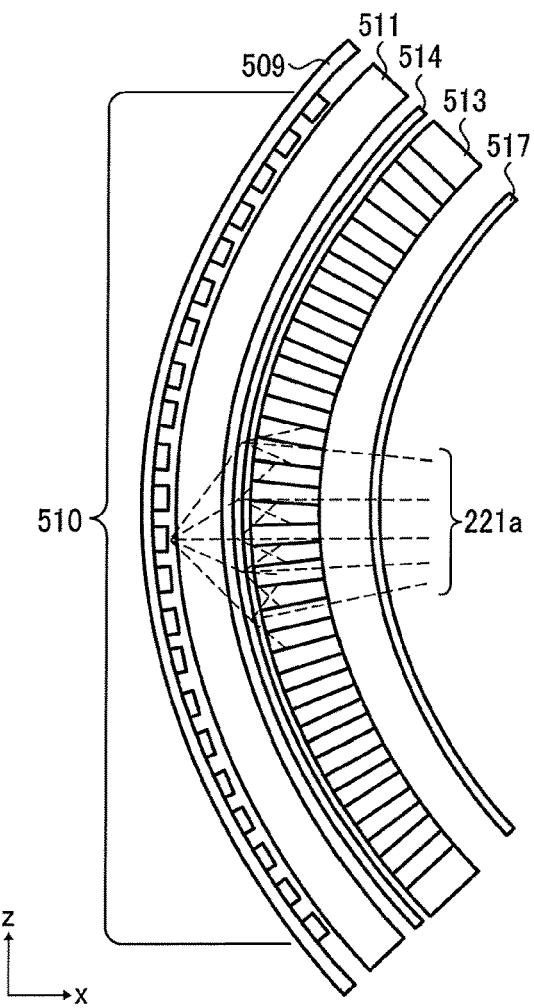
FIG. 4 is a plan view illustrating the mechanical configuration of the lighting device for gloss according to the present embodiment.

FIG. 4 is a diagram illustrating an example of a mechanical configuration of the lighting device for gloss 211 according to the present embodiment, and illustrates a plan view seen through an internal structure of the lighting device for gloss 211. Note that FIG. 4 mainly illustrates members involved in emission of light in the internal structure of the lighting device for gloss 211.

The bases 501a and 501b are members constituting a casing of the lighting device for gloss 211. The base 501a constitutes a casing on an upper side of the lighting device for gloss 211, and the base 501b constitutes a casing on a lower side of the lighting device for gloss 211. In a space constituted by the bases 501a and 501b, other constituent elements of the lighting device for gloss 211 are disposed.

The spacer 503 is disposed so as to be sandwiched between the base 501a and the base 501b in order to secure a space between the base 501a and the base 501b.

The power supply substrate 504 is a power supply for the lighting device for gloss 211 and supplies power to the flexible substrate 509 on which the LEDA 510 is disposed via the connector 505.

The connector 505 is a connector for electrically coupling the power supply substrate 504 to the flexible substrate 509.

The base plate 506 is a plate for supporting the flexible substrate 509, and is secured to the base 501a by the shim 507a and secured to the base 501b by the shim 507b.

The shim 507a is a wedge for securing the base plate 506 to the base 501a. The shim 507b is a wedge for securing the base plate 506 to the base 501b.

The radiator 508 radiates heat generated by the LEDA 510, and is disposed on a surface of the base plate 506 opposite to the surface on which the LEDA 510 (flexible substrate 509) is disposed.

The flexible substrate 509 is a deformable substrate for supporting the LEDA 510, and is supported by the base plate 506.

The LEDA 510 is a light source in which a plurality of LED chips (an example of light emitting elements) is arranged. The LEDA 510 (LED chips) emits light based on supply of power from the power supply substrate 504, and emits illumination light (more specifically, diffusion illumination light). In the present embodiment, the flexible substrate 509 supports the LEDA 510 (LED chips). Therefore, the LEDA 510 (LED chips) is arranged in a shape in which the flexible substrate 509 is deformable. As illustrated in FIG. 4, the LEDA 510 is formed by curving and arranging a plurality of LED chips. In FIG. 4, the LEDA 510 is formed by arranging the plurality of LED chips in a curved surface shape with a first curvature.

The rod lens 511 corrects an optical path such that the illumination light emitted from the LEDA 510 is guided into the honeycomb member 513 as much as possible. In particular, the rod lens 511 corrects the optical path of the illumination light emitted from the LEDA 510 in a vertical direction (y direction). In the present embodiment, a case where the optical path of the illumination light emitted from the LEDA 510 is corrected by a rod lens method using the rod lens 511 will be exemplified. However, the present embodiment is not limited thereto, and a reflector method or a cylindrical lens method may be used.

The lens supports 512a and 512b are members for securing the rod lens 511 to a predetermined position.

The diffusion transmission film 514 is bonded to a surface of the honeycomb member 513 on a side of the rod lens 511 (a surface on which the illumination light emitted from the LEDA 510 is incident), diffuses and transmits the illumination light emitted from the LEDA 510, and sends out the illumination light into the honeycomb member 513.

The specular reflection film 515a is bonded to an upper portion of a surface of the diffusion transmission film 514 on a side of the rod lens 511 (a surface on which the illumination light emitted from the LEDA 510 is incident), and the specular reflection film 515b is bonded to a lower portion of a surface of the diffusion transmission film 514 on a side of the rod lens 511 (a surface on which the illumination light emitted from the LEDA 510 is incident).

The specular reflection films 515a and 515b reflect illumination light having an optical path that has not been corrected, so as to be guided into the honeycomb member 513 by the rod lens 511. As a result, the optical path is again corrected such that the reflected illumination light is guided into the honeycomb member 513 by the rod lens 511, that is, effective utilization of the illumination light can be expected.

The honeycomb member 513 is a member having an extendable and contractible honeycomb structure, disposed in a curved surface shape with a second curvature larger than the first curvature in an emission direction of the illumination light of the LEDA 510. The LEDA 510 and the honeycomb member 513 are both curved in a longitudinal direction of the honeycomb member 513 (that is, in the direction in which the plurality of LED chips is arranged), while sharing the common center of curvature. The honeycomb member 513 may include any material, and examples thereof include a material such as aluminum or paper. In the present embodiment, by adjusting extendibility of the honeycomb structure (shape of the honeycomb structure) of the honeycomb member 513, the degree of parallelism with an x direction on an xz plane can be adjusted to output the illumination light from the honeycomb member 513 in a specified direction.

That is, the honeycomb member 513 according to the present embodiment functions as a louver. How the honeycomb member 513 is used to adjust the degree of parallelism with the x direction on the xz plane to output the illumination light in a specified direction will be described later.

The dustproof film 517 is a film for preventing intrusion of dust and the like into the lighting device for gloss 211.

The light shielding films 518a and 518b shield at least a part of illumination light which has passed through the honeycomb member 513 in the longitudinal direction of the honeycomb member 513. The light shielding film 518a (an example of a first light shielding member) is bonded to an upper portion of a surface of the dustproof film 517 on a side of the honeycomb member 513 (a surface on which the illumination light which has passed through the honeycomb member 513 is incident). The light shielding film 518a shields illumination light which has passed through an upper side of the honeycomb member 513 in a lateral direction (y direction) that is orthogonal to the longitudinal direction, in the longitudinal direction (z direction) of the honeycomb member 513. The light shielding film 518b (an example of a second light shielding member) is bonded to a lower portion of a surface of the dustproof film 517 on a side of the honeycomb member 513 (a surface on which the illumination light which has passed through the honeycomb member 513 is incident). The light shielding film 518b shields illumination light which has passed through a lower side of the honeycomb member 513 in a lateral direction (y direction) thereof, in the longitudinal direction of the honeycomb member 513.

In the present embodiment, by adjusting a distance between the light shielding films 518a and 518b (the degree of opening of the dustproof film 517), the degree of parallelism with the x direction on the xy plane is adjusted to output the illumination light in a specified direction (in detail, to emit the illumination light from the lighting device for gloss 211 as the above-described illumination light 221a). How the light shielding films 518a and 518b are used to adjust the degree of parallelism with the x direction on the xy plane to output the illumination light in a specified direction will be described later.

A reading area of the printed matter P is irradiated with the illumination light which has passed through the honeycomb member 513, and through the dustproof film 517 without being shielded by the light shielding films 518a and 518b, as the above-described illumination light 221a.

Figure 5:
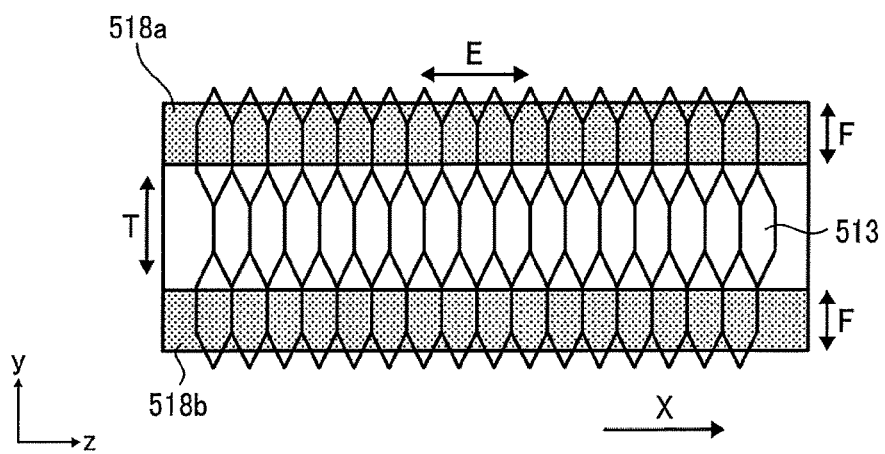
FIG. 5 is an illustration for explaining a mechanism to adjust the degree of parallelism to output illumination light in a specified direction by using a honeycomb member and a light shielding film according to the embodiment.
Figure 6:
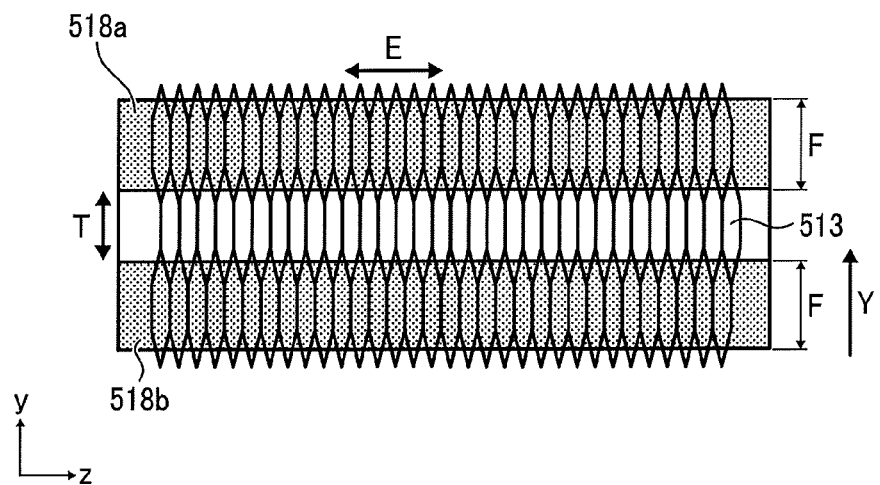
FIG. 6 is an illustration for explaining a mechanism to adjust the degree of parallelism to output illumination light in a specified direction by using a honeycomb member and a light shielding film according to the present embodiment.

FIGS. 5 and 6 are illustration for explaining a mechanism to adjust the degree of parallelism to output the illumination light in a specified direction by using the honeycomb member 513 and the light shielding films 518a and 518b. The honeycomb member 513 in FIGS. 5 and 6 has the same longitudinal direction as a main scanning direction X. In FIGS. 5 and 6, Y represents a sub-scanning direction. The z direction is a direction corresponding to the main scanning direction X. The y direction is a direction corresponding to the sub-scanning direction Y. F indicates a range shielded from light by the film 518a or 518b.

For example, as illustrated in FIG. 5, in a case where the honeycomb member 513 is extended in the z direction which is the longitudinal direction of the honeycomb member 513, the degree of opening of each honeycomb in the z direction (the degree of extension indicated by arrow E) increases. Therefore, not only illumination light having the high degree of parallelism with the x direction on the xz plane but also illumination light having the slightly lower degree of parallelism with the x direction can be output from the honeycomb member 513 in a specified direction.

On the other hand, as illustrated in FIG. 6, in a case where the honeycomb member 513 is contracted in the z direction which is the longitudinal direction of the honeycomb member 513, the degree of opening of each honeycomb in the z direction (the degree of extension indicated by arrow E) decreases. Therefore, only illumination light having the high degree of parallelism with the x direction on the xz plane can be output from the honeycomb member 513 in a specified direction. Illumination light having the slightly lower degree of parallelism with the x direction is not output from the honeycomb member 513 in a specified direction.

As described above, in the present embodiment, as the degree of opening of each honeycomb in the z direction becomes smaller, illumination light output from the honeycomb member 513 in a specified direction can be limited to light with the high degree of parallelism (degree of parallelism with the x direction on the xz plane). As the degree of opening of each honeycomb in the z direction becomes larger, illumination light output from the honeycomb member 513 in a specified direction includes light having the slightly lower degree of parallelism (degree of parallelism with the x direction on the xz plane).

In other words, in the present embodiment, by adjusting the degree of opening of each honeycomb in the z direction, the degree of parallelism is adjusted with respect to a main scanning direction of the printed matter P for illumination light used as the illumination light 221a incident on a reading area of the printed matter P.

Further, as illustrated in FIG. 5, in a case where the distance between the light shielding films 518a and 518b is large, the degree of opening of the dustproof film 517 in the y direction is large. Therefore, not only illumination light having the high degree of parallelism with the x direction on the xy plane but also illumination light having the slightly lower degree of parallelism with the x direction can also be output in a specified direction. That is, an illumination light transmission region T in FIG. 5 becomes relatively large.

On the other hand, as illustrated in FIG. 6, in a case where the distance between the light shielding films 518a and 518b is small, the degree of opening of the dustproof film 517 in the y direction is small. Therefore, only illumination light having the high degree of parallelism with the x direction on the xy plane can be output in a specified direction, and illumination light having the slightly lower degree of parallelism with the x direction cannot be output in the specified direction. That is, the illumination light transmission region T becomes relatively small.

As described above, in the present embodiment, as the distance between the light shielding films 518a and 518b becomes smaller, illumination light output in a specified direction can be limited to light having the higher degree of parallelism (degree of parallelism with the x direction on the xy plane). As the distance between the light shielding films 518a and 518b becomes larger, the illumination light output in the specified direction includes also light having the slightly lower degree of parallelism (degree of parallelism with the x direction on the xy plane).

That is, in the present embodiment, by adjusting the distance between the light shielding films 518a and 518b, the degree of parallelism is adjusted with respect to a sub-scanning direction of the printed matter P for illumination light used as the illumination light 221a incident on a reading area of the printed matter P.

Next, an advantage of being able to adjust the degree of parallelism of the illumination light 221a emitted from the lighting device for gloss 211 will be described.

As described in the related art, a conventional lighting device is designed on the premise that a surface of an object on which substantially parallel light is incident has a specific degree of flatness (usually a complete plane). That is, the conventional lighting device is designed such that the degree of parallelism of substantially parallel light is as high as possible. Therefore, in a case where the surface of the object is a non-perfect plane having waviness or inclination, regularly reflected light from the object does not sufficiently enter a target area (reduction optical system).

Figure 7:
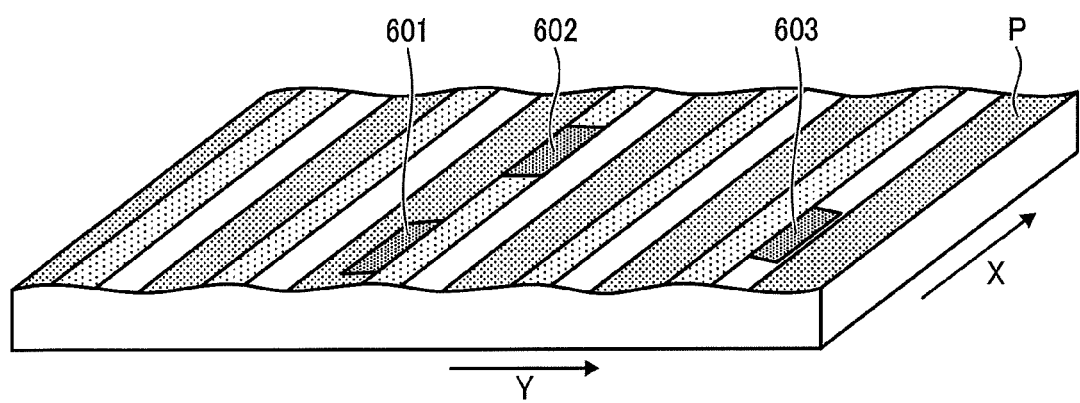
FIG. 7 is a diagram illustrating an example of a printed matter according to the present embodiment.

For example, as illustrated in FIG. 7, it is assumed that a printed surface of the printed matter P according to the present embodiment is a non-perfect plane having waviness. Note that gloss defects (low gloss portions) 601 to 603 are present in the printed matter P.

The conventional lighting device is designed such that, in a case where the degree of parallelism of substantially parallel light is extremely high and an incident surface of the substantially parallel light is a perfect plane, regularly reflected light of the substantially parallel light is incident to the reduction optical system. Therefore, in a case of the printed matter P as illustrated in FIG. 7, due to the waviness of the printed surface, the regularly reflected light of the substantially parallel light does not sufficiently enter the reduction optical system.

Figure 8:
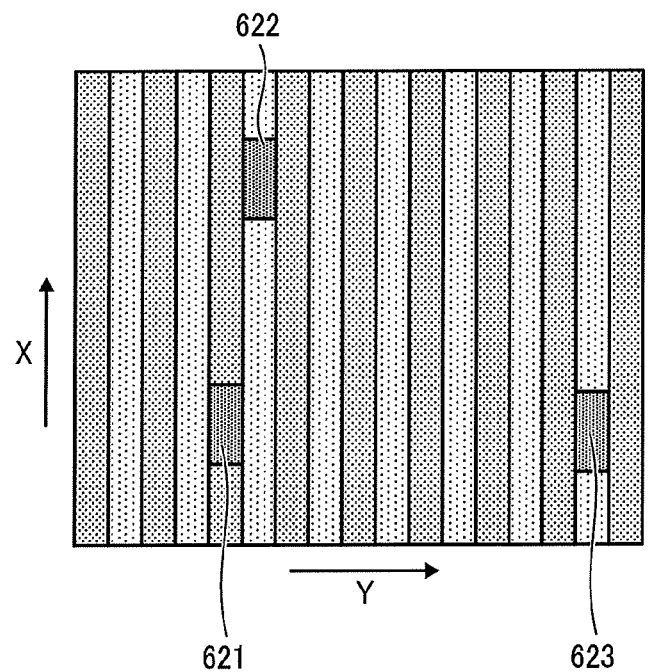
FIG. 8 is a diagram illustrating an example of a read image for inspecting a gloss defect in Comparative Example.

For this reason, in a case of using the conventional lighting device, a read image for inspection of a gloss defect generated based on regularly reflected light directed to the reduction optical system includes, as illustrated in FIG. 8, an image of a waviness (non-perfect plane) portion darker than a non-waviness (perfect plane) portion because the regularly reflected light in the waviness (non-perfect plane) portion does not sufficiently enter the reduction optical system.

As a result, defect images 622 and 623 corresponding to gloss defects (low gloss portions) 602 and 603 present in the non-waviness (perfect plane) portion are easily observed without being darkened. However, a defect image 621 corresponding to a gloss defect (low gloss portion) 601 present in the waviness (non-perfect plane) portion is darkened, and is not easily observed. Therefore, even when a gloss defect is inspected using a read image as illustrated in FIG. 8, it is difficult to inspect (detect) a gloss defect present in the waviness (non-perfect plane) portion with high accuracy.

In contrary, as described above, the lighting device for gloss 211 according to the present embodiment can adjust the degree of parallelism of the illumination light 221a emitted from the lighting device for gloss 211. Therefore, in the present embodiment, the degree of parallelism of illumination light used as the illumination light 221a is adjusted according to the degree of flatness of the printed matter P. Specifically, adjustment is performed such that only illumination light having a high degree of parallelism is used as the illumination light 221a as the plane of the printed matter P is closer to a perfect plane (as the degree of flatness is higher). On the other hand, adjustment is performed such that the illumination light 221a includes also illumination light having the slightly lower degree of parallelism as the plane of the printed matter P is less perfect (as the degree of flatness is lower). Such adjustment is made by an inspector, for example.

For example, as illustrated in FIG. 7, in a case where a printed surface of the printed matter P according to the present embodiment is a non-perfect plane having waviness, as clear from the above description, an increase in the degree of parallelism of the illumination light 221a makes it difficult to perform inspection (detection) with high accuracy.

Therefore, in the present embodiment, the degree of parallelism of illumination light used as the illumination light 221a is adjusted according to the degree of flatness of the printed matter P. Specifically, as for the waviness (non-perfect plane) of the printed matter P in a sub-scanning direction, the distance between the light shielding films 518a and 518b is adjusted such that the illumination light 221a includes also illumination light having the degree of parallelism corresponding to the waviness in the sub-scanning direction. As for the waviness (non-perfect plane) of the printed matter P in a main scanning direction, the degree of opening of each honeycomb in the z direction of the honeycomb member 513 is adjusted such that the illumination light 221a includes also illumination light having the degree of parallelism corresponding to the waviness in the main scanning direction.

Figure 9:
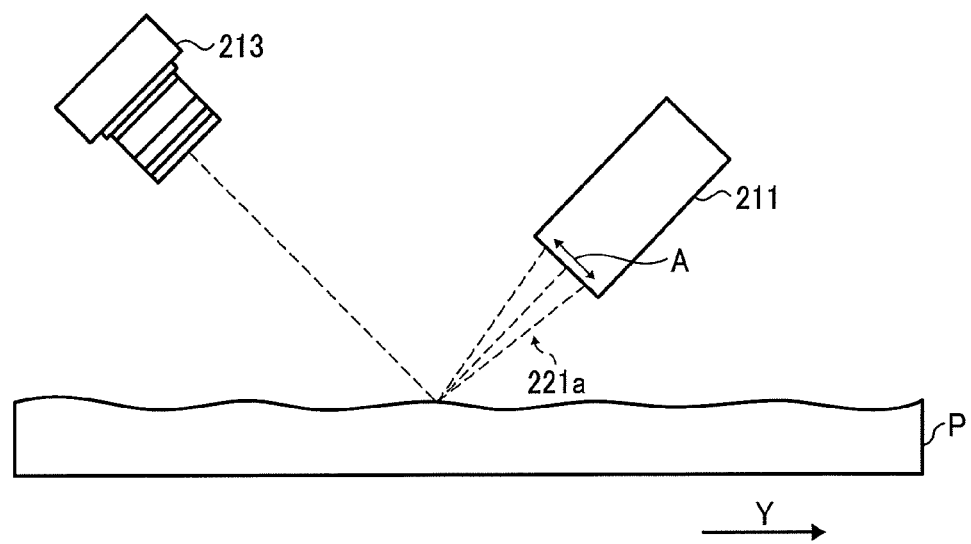
FIG. 9 is an illustration for explaining a mechanism to sufficiently direct regularly reflected light from a non-perfect plane to an image sensor by adjusting the degree of parallelism of illumination light according to the present embodiment.
Figure 10:
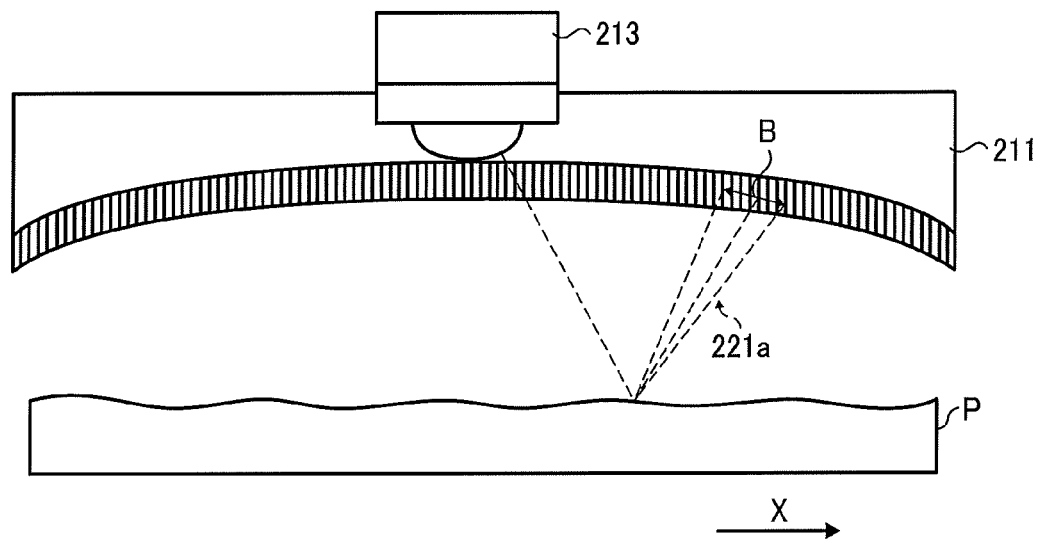
FIG. 10 is an illustration for explaining a mechanism to sufficiently direct regularly reflected light from a non-perfect plane to an image sensor by adjusting the degree of parallelism of illumination light according to the present embodiment.

FIGS. 9 and 10 are illustration for explaining how the degree of parallelism of the illumination light 221a can be adjusted to cause regularly reflected light from a non-perfect plane to sufficiently enter the image sensor 213.

For example, it is assumed that the distance between the light shielding films 518a and 518b is adjusted such that the illumination light 221a includes also illumination light having the degree of parallelism corresponding to the waviness of the printed matter P in the sub-scanning direction. In this case, as illustrated in FIG. 9, regularly reflected light of the illumination light 221a emitted from a point within width A corresponding to the distance between the light shielding films 518a and 518b is directed to the image sensor 213.

Specifically, illumination light having various degrees of parallelism is emitted from each point within width A as the illumination light 221a. A reading area of the printed matter P is irradiated with illumination light having the degree of parallelism corresponding to each point, and regularly reflected light is directed to the image sensor 213. For example, the reading area of the printed matter P is irradiated with illumination light emitted from a center point of width A, having the high degree of parallelism, and regularly reflected light is directed to the image sensor 213. For example, the reading area of the printed matter P is irradiated with illumination light emitted from a point far away from the center point of width A, having the slightly lower degree of parallelism, and regularly reflected light is directed to the image sensor 213.

Further, it is assumed that the degree of opening of each honeycomb in the z direction of the honeycomb member 513 is adjusted such that the illumination light 221a includes also illumination light having the degree of parallelism corresponding to the waviness of the printed matter P in the main scanning direction. In this case, as illustrated in FIG. 10, regularly reflected light of the illumination light 221a emitted from a point within width B corresponding to the degree of opening of a honeycomb can be directed to the image sensor 213.

In this embodiment, extendibility of the honeycomb structure (shape of the honeycomb structure) of the honeycomb member 513 can be freely adjusted. However, extendibility of the honeycomb structure may be kept the same after installation of the lighting device for gloss 211 on the reader 201. Further, extendibility of the honeycomb structure (shape of the honeycomb structure) of the honeycomb member 513 may be adjusted by a user (inspector) according to characteristics of the recording medium (recording sheet) having the image to be inspected. Alternatively, extendibility of the honeycomb structure may be automatically set, according to characteristics of the recording medium having the image to be inspected, for example, based on statistical data indicating correspondence between the extendibility and the flatness of the recording medium. The extendibility of the honeycomb structure (shape of the honeycomb structure) of the honeycomb member 513 may be previously adjusted, before use by the user (inspector).

Specifically, illumination light having various degrees of parallelism is emitted from each point within width B as the illumination light 221a. A reading area of the printed matter P is irradiated with illumination light having the degree of parallelism corresponding to each point, and regularly reflected light is directed to the image sensor 213. For example, the reading area of the printed matter P is irradiated with illumination light emitted from a center point of width B, having the high degree of parallelism, and regularly reflected light is directed to the image sensor 213. Further, in this example, the reading area of the printed matter P is irradiated with illumination light emitted from a point far away from the center point of width B, having the slightly lower degree of parallelism, and regularly reflected light is directed to the image sensor 213.

Figure 11:
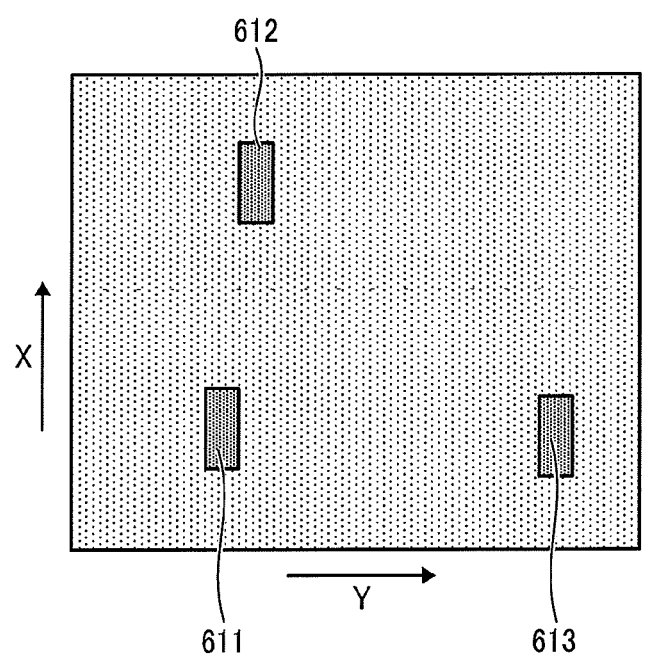
FIG. 11 is a diagram illustrating an example of a read image for inspecting a gloss defect according to the present embodiment.

As described above, in the present embodiment, like the printed matter P illustrated in FIG. 7, even if waviness is present (even in a case of a non-perfect plane), regularly reflected light of the illumination light 221a can be sufficiently directed to the image sensor 213. For this reason, in a read image for inspection of a gloss defect generated based on regularly reflected light directed to the image sensor 213, regularly reflected light in the waviness (non-perfect plane) is also sufficiently directed to the image sensor 213, and as illustrated in FIG. 11, the non-waviness (perfect plane) portion and the waviness (non-perfect plane) portion are images having constant brightness.

As a result, not only defect images 612 and 613 corresponding to the gloss defects (low gloss portions) 602 and 603 present in the non-waviness (perfect plane) portion but also a defect image 611 corresponding to a gloss defect (low gloss portion) 601 present in the waviness (non-perfect plane) portion is easily observed. Therefore, if a gloss defect is inspected using a read image as illustrated in FIG. 11, a gloss defect present in the waviness (non-perfect plane) portion can be also inspected (detected) with high accuracy.

Next, an experimental result will be described, which indicates that the degree of parallelism of the illumination light 221a can be adjusted by adjusting the degree of opening of each honeycomb in the z direction of the honeycomb member 513 according to the present embodiment.

Figure 12:
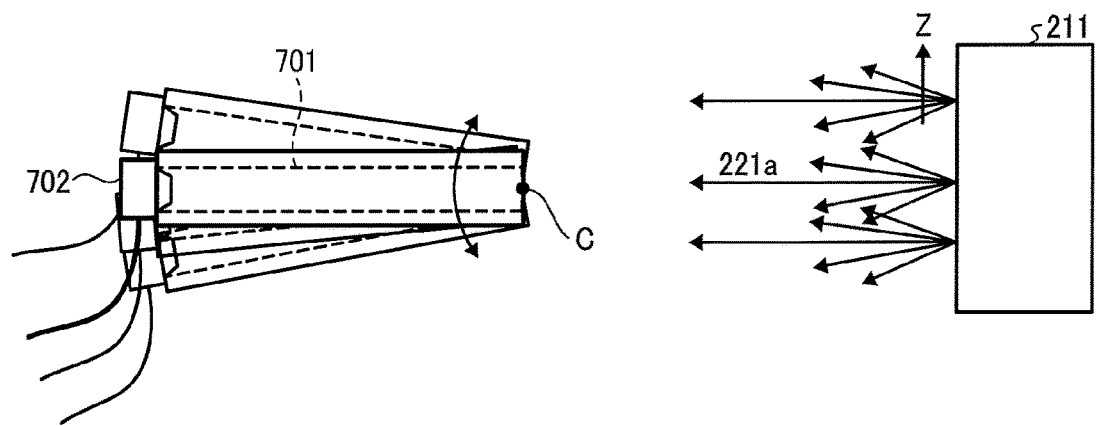
FIG. 12 is a diagram illustrating an example of a measurement experiment of illuminance according to the present embodiment.

In the present embodiment, as illustrated in FIG. 12, illuminance of the illumination light 221a emitted from the lighting device for gloss 211 is measured using a measuring device having an illuminance meter 702 disposed at one end of a cylinder 701. The measuring device is placed in an arbitrary distance from the lighting device for gloss 211. Specifically, while the cylinder 701 is rotated up and down with the other end of the cylinder 701 (the end where the illuminance meter 702 is not disposed) about a rotation center C, illuminance of the illumination light 221a incident from the other end of the cylinder 701 is measured using the illuminance meter 702.

Figure 13:
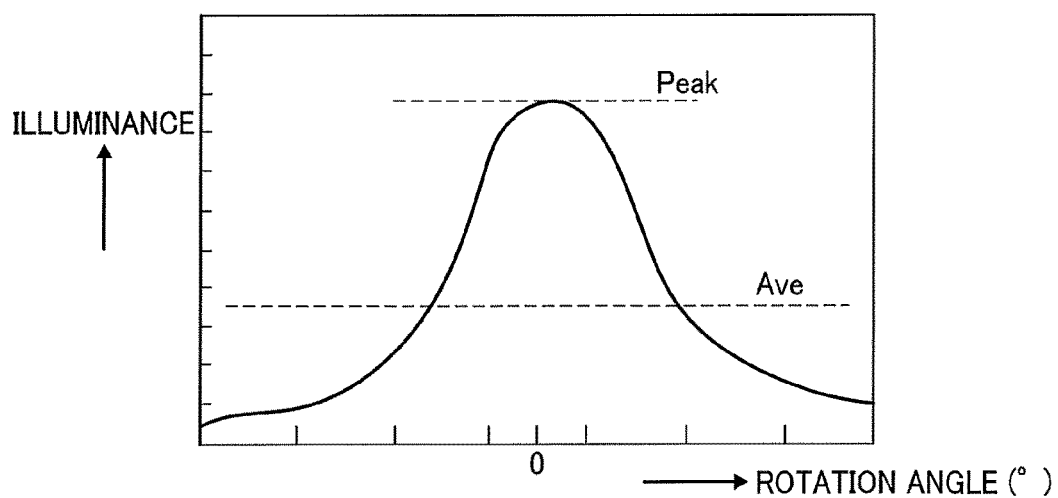
FIG. 13 is a graph illustrating an example of results of a measurement experiment of illuminance according to the present embodiment.

FIG. 13 illustrates measurement results of the illuminance, measured using the illuminance meter 702. As illustrated in FIG. 13, as a rotation angle of the cylinder 701 is closer to 0, the measured illuminance becomes higher. As the rotation angle of the cylinder 701 is farther from 0, the measured illuminance becomes lower. Referring to the graph in FIG. 13, as the degree of parallelism of the illumination light 221a becomes higher, the peak in illuminance becomes high, such that the illuminance tends to suddenly decrease as the rotation angle of the cylinder 701 becomes far from 0. This will be explained below referring to FIG. 14.

Figure 14:
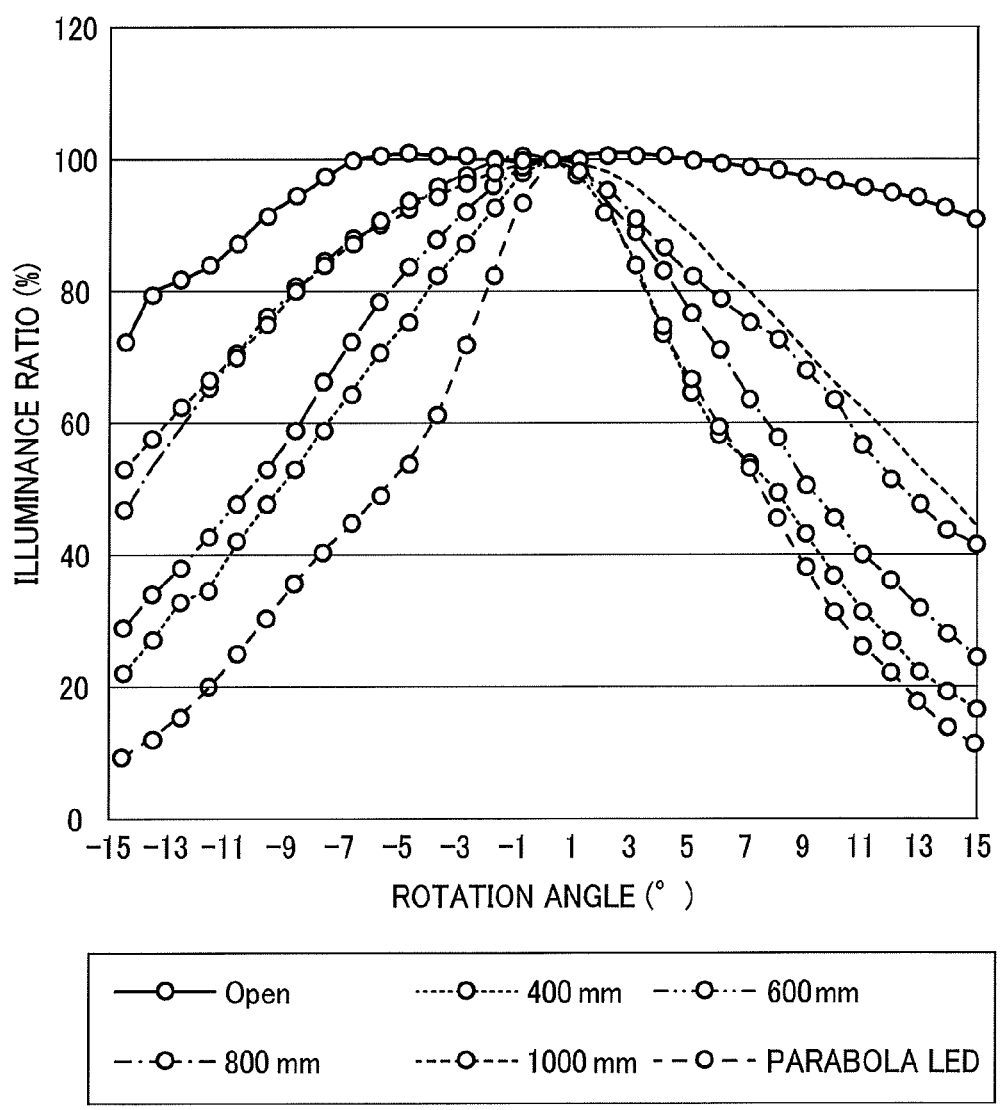
FIG. 14 is a graph illustrating an example of results of a measurement experiment of illuminance according to the present embodiment.

FIG. 14 is a graph illustrating results of a measurement experiment of illuminance. More specifically, FIG. 14 illustrates measurement results of illuminance under six conditions including: Open (the honeycomb member 513 is not disposed), the degree of opening of each honeycomb adjusted to 400 mm, the degree of opening of each honeycomb adjusted to 600 mm, the degree of opening of each honeycomb adjusted to 800 mm, the degree of opening of each honeycomb adjusted to 1000 mm, and a parabolic LED (lighting device described in related art). In FIG. 14, the X axis corresponds to a ratio of illuminance represented by percentage, for the ease of comparison between these different conditions.

The results illustrated in FIG. 14 indicate that the illuminance in the case where the rotation angle of the cylinder 701 is far from 0 is lower as the degree of opening of each honeycomb is smaller, and that the degree of parallelism of the illumination light 221a is higher as the degree of opening of each honeycomb is smaller. The results illustrated in FIG.

14 further indicate that the illuminance of the illumination light 221a in a case where the degree of opening of each honeycomb is adjusted to 400 mm is at a level close to illuminance of illumination light of the lighting device described in related art, thus, achieving the degree of parallelism close to that of the lighting device described in related art.

Next, a hardware configuration of the inspection apparatus 200 according to the present embodiment will be described. FIG. 15 is a block diagram illustrating an example of a hardware configuration of the inspection apparatus 200 according to the present embodiment. As illustrated in FIG. 15, the inspection apparatus 200 has a configuration in which a controller 910 is coupled to an engine 960 via a protocol control information (PCI) bus. The controller 910 is a controller for controlling the entire operation to be performed by the inspection apparatus 200, such as rendering, communication, and input from a control panel 920. The engine 960 is an engine connectable to the PCI bus, and is, for example, a scanner engine such as a scanner. In addition to an engine section, the engine 960 may include an image processing section that performs such as error diffusion or gamma conversion. However, as long as the engine 960 operates as the reader 201 that reads the light level, other processing such as image processing and communication does not have to be provided.

The controller 910 includes a central processing unit (CPU) 911, a north bridge (NB) 913, a system memory (MEM-P) 912, a south bridge (SB) 914, a local memory (MEM-C) 917, an ASIC 916, and a hard disk drive (I-EDD) 918, and has a configuration in which the north bridge (NB) 913 is coupled to the ASIC 916 by an Accelerated Graphics Port (AGP) bus 915. The MEM-P 912 further includes a read-only memory (ROM) 912a and a random-access memory (RAM) 912b.

The CPU 911 controls the entire inspection apparatus 200. The CPU 911 includes a chip set including an NB 913, an MEM-P912, and an SB 914, and is coupled to another apparatus via this chip set.

The NB 913 is a bridge for coupling the CPU 911 to the MEM-P912, the SB 914, and the AGP bus 915, and includes a memory controller for controlling reading and writing to the MEM-P 912, a PCI master, and an AGP target.

The MEM-P 912 is a system memory used as a memory for storing a program and data, a memory for developing a program and data, a drawing memory for a printer, and the like, and includes the ROM 912a and the RAM 912b. The ROM 912a is a read-only memory used as a memory for storing a program and data. The RAM 912b is a writable and readable memory used as a memory for developing a program and data, a drawing memory for a printer, and the like.

The SB 914 is a bridge for coupling the NB 913 to a PCI device or a peripheral device. The SB 914 is coupled to the NB 913 via the PCI bus, and a network interface (I/F) and the like are also coupled to this PCI bus.

The ASIC 916 is an IC having a hardware element for image processing and used for image processing, and functions as a bridge coupling each of the AGP bus 915, the PCI bus, the HDD 918, and the MEM-C917. The ASIC 916 includes a PCI target and an AGP master, an arbiter (ARB) forming a core of the ASIC 916, a memory controller for controlling the MEM-C917, a plurality of direct memory access controllers (DMACs) for rotating image data and the like by hardware logic and the like, and a PCI unit for transferring data to and from the engine 960 via the PCT bus. To this ASIC 916, a USB 940 and an IEEE 1394 interface (I/F) 950 are coupled via the PCI bus. The control panel 920 is directly coupled to the ASIC 916.

The MEM-C917 is a local memory used as a copy image buffer and a code buffer. The HDD 918 is a storage for storing image data, storing a program, storing font data, and storing a form.

The AGP bus 915 is a bus interface for a graphics accelerator card proposed for speeding up graphics processing, and directly accesses the MEM-P912 with high throughput to speed up the graphics accelerator card.

The image forming apparatus 100 has a hardware configuration that is substantially similar to the hardware configuration of the inspection apparatus 200 illustrated in FIG. 15, except some differences. Such differences include addition of a print engine as a part of the engine 960, which controls print processing. Specifically, the print engine controls print processing, using the photoconductor drums 103Y, 103M, 103C, 103K, and 103 CL, the transfer belt 105, the secondary transfer roller 107, the paper feeder 109, the conveying roller pair 111, and the fixing device 113.

Figure 16:
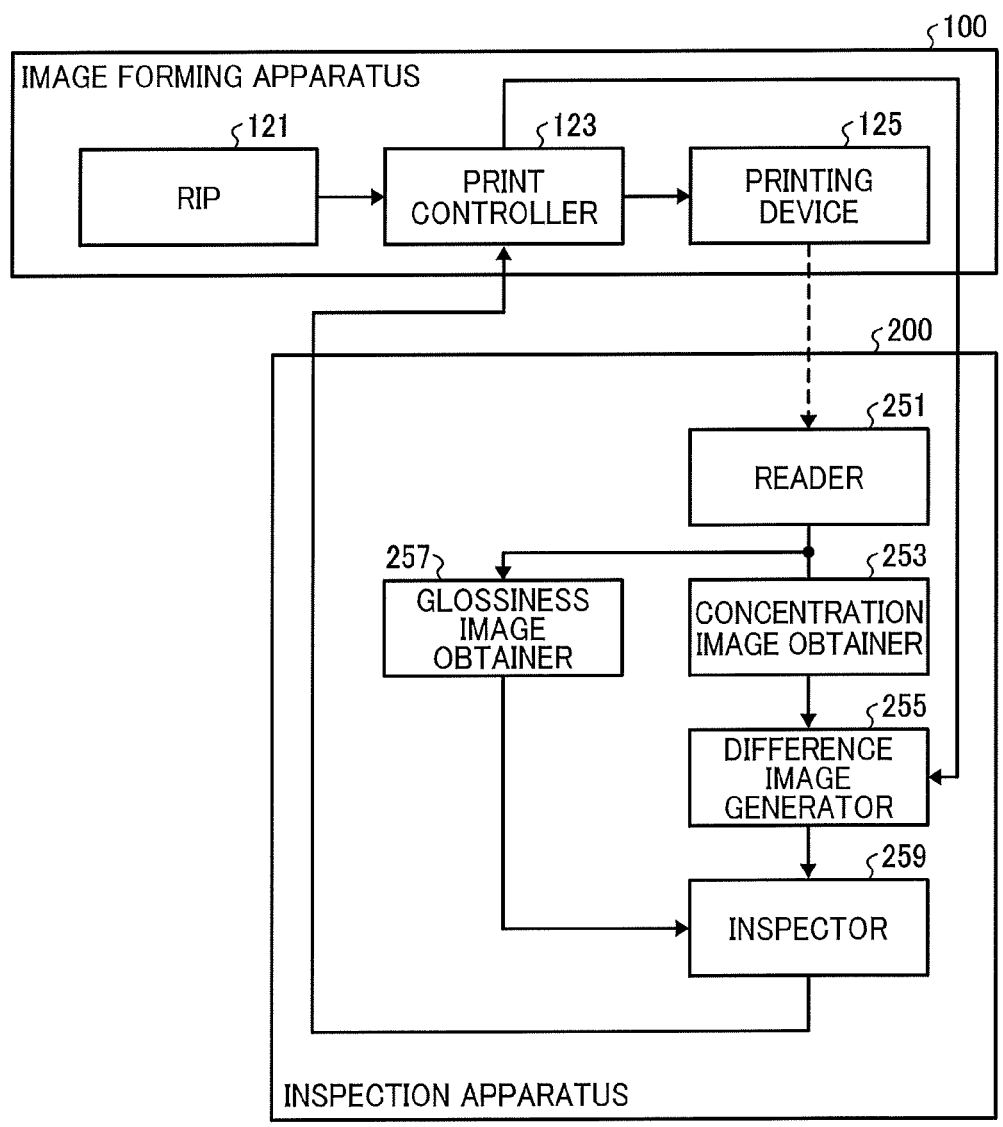
FIG. 16 is a block diagram illustrating an example of a functional configuration of an image forming apparatus and the inspection apparatus according to the present embodiment.

FIG. 16 is a block diagram illustrating an example of a functional configuration of the image forming apparatus 100 and the inspection apparatus 200 according to the present embodiment. As illustrated in FIG. 16, the image forming apparatus 100 includes a raster image processor (RIP) 121, a print controller 123, and a printing device 125. The inspection apparatus 200 includes a reader 251, a concentration image obtainer 253, a difference image generator 255, a glossiness image obtainer 257, and an inspector 259.

In the present embodiment, a case where the image forming apparatus 100 includes the RIP 121 will be exemplified. However, the present embodiment is not limited thereto, and a device different from the image forming apparatus 100, such as a digital front end (DFE), may include the RIP 121.

In the present embodiment, it is assumed that the image forming apparatus 100 is coupled to the inspection apparatus 200 via a local interface such as a universal serial bus (USB) or a peripheral component interconnect express (PCIe). However, a connection between the image forming apparatus 100 and the inspection apparatus 200 is not limited thereto.

The RIP 121 and the print controller 123 are implemented by, for example, the CPU 911. The printing device 125 is implemented by, for example, the image forming device capable of forming the image such as the photoconductor drums 103Y, 103M, 103C, 103K, and 103CL, the transfer belt 105, the secondary transfer roller 107, and the fixing device 113, but is not limited thereto. As described above, in the present embodiment, an image is printed by an electrophotographic method, but the present embodiment is not limited thereto, and the image may be printed by an inkjet method.

The reader 251, which corresponds to the reader 201, is implemented by, for example, the engine 960 such as the scanner engine. The concentration image obtainer 253 and the glossiness image obtainer 257 are implemented by, for example, the CPU 911 and the system memory 912. The difference image generator 255 and the inspector 259 may be implemented by, for example, the CPU 911 and the system memory 912, and/or the ASIC 916 or the like.

The RIP 121 receives print data from an external device such as a host device, subjects the received print data to RIP processing, and generates a RIP image. In the present embodiment, the print data includes job information described in a page description language (PDL) such as PostScript (registered trademark), image data in a tagged image file format (TIFF), and the like, but is not limited thereto. In the present embodiment, the RIP image is CMYK RIP image data, but is not limited thereto.

The print controller 123 transmits the RIP image generated by the RIP 121 to the printing device 125, and transmits the RIP image to the inspection apparatus 200.

The printing device 125 forms an image on a recording medium (sheet) based on the RIP image to generate a printed matter.

The reader 201 reads the printed matter as an inspection target printed (generated) by the printing device 125, generates a concentration image indicating the concentration of the printed matter and a glossiness image indicating the glossiness of the printed matter.

Specifically, the lighting device for concentration 212 of the reader 201 irradiates the printed matter as an inspection target with the illumination light 222a, and the image sensor 213 of the reader 201 reads the diffusion reflection light 222b reflected by the printed matter as an inspection target. Based on the detected light level, a concentration image is generated. Similarly, the lighting device for gloss 211 of the reader 201 irradiates the printed matter as an inspection target with the illumination light 221a, and the image sensor 213 of the reader 201 reads the regularly reflected light 221b reflected by the printed matter as an inspection target. Based on the detected light level, a glossiness image is generated. In the present embodiment, the concentration image and the glossiness image are RGB image data, but are not limited thereto.

The concentration image obtainer 253 acquires the concentration image generated by the reader 201.

The difference image generator 255 acquires a RIP image from the image forming apparatus 100, and generates a reference image (master image) based on the acquired RIP image. Specifically, the difference image generator 255 acquires a RIP image of each of C, M, Y, and K from the image forming apparatus 100 (print controller 123), applies various image processing such as multi-level conversion processing, smoothing processing, resolution conversion processing, and color conversion processing, to the acquired RIP image of each of C, M, Y, and K, to generate a reference image. In the present embodiment, the reference image is RGB image data, but is not limited thereto.

Then, the difference image generator 255 generates a difference image indicating a difference between the generated reference image and the concentration image acquired by the concentration image obtainer 253. Specifically, the difference image generator 255 compares the reference image with the concentration image in a pixel unit, calculates a difference value of pixel values of each of the RGB colors for each pixel, and generate a difference image constituted by the difference value of the pixel values for each pixel.

The glossiness image obtainer 257 acquires a glossiness image (for example, a read image as illustrated in FIG. 11) generated by the reader 201.

The inspector 259 inspects a printed matter based on the glossiness image acquired by the glossiness image obtainer 257.

Figure 17:
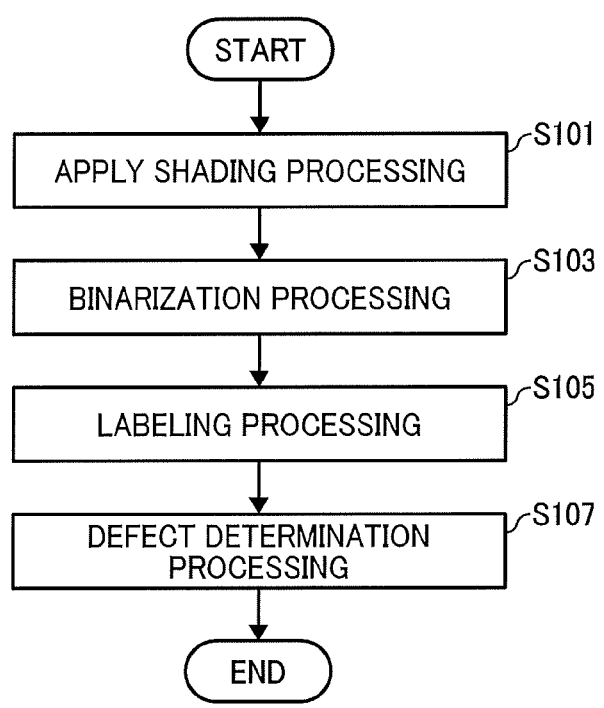
FIG. 17 is a flowchart illustrating an example operation of inspecting gloss of the printed matter, performed by the inspection apparatus, according to the present embodiment.

FIG. 17 is a flowchart illustrating operation of inspecting gloss of the printed matter, performed by the inspection apparatus 200, according to the present embodiment. Further, in this example, it is assumed that the initial paper is used to print an image thereon.

First, the inspector 259 cuts out an image corresponding to a specific reading time period, from the glossiness image acquired by the glossiness image obtainer 257, and applies shading processing to the cut-out image (step S101). For example, the inspector 259 calculates an average value of pixel values in each pixel column in a sub-scanning direction for the cut-out image, calculates a coefficient of each pixel column such that the average value is a constant value in each pixel column, multiplies each of pixel values of pixels constituting each pixel column by the coefficient of the pixel column, and thereby subjects the cut-out image to shading processing. Thermal paper is basically white. Therefore, if it is set that the thermal paper has a constant reflectance over the entire area, illumination intensity unevenness is corrected by this shading processing.

Subsequently, the inspector 259 binarizes the image to which shading processing is applied, with a specified threshold value (step S103). A defective portion of thermal paper occurs in a black side (low gloss portion). Therefore, here, a portion having a specified image signal value or less is binarized and extracted.

Subsequently, the inspector 259 labels the image to which binarization processing is applied (step S105). Specifically, the inspector 259 performs numbering and feature amount extraction on each portion extracted in binarization processing. As the feature amount, at least one of the area, the peripheral length, the aspect ratio, and the like of the portion extracted in binarization processing can be mentioned, but the feature amount is not limited thereto.

Subsequently, the inspector 259 compares the feature amount of each portion which has been subjected to labeling processing with a threshold value for glossiness inspection, and performs defect determination processing of inspecting a gloss defect of a printed matter (step S107).

Furthermore, the inspector 259 inspects the printed matter based on the difference image generated by the difference image generator 255. For example, the inspector 259 inspects a concentration defect of the printed matter generated by the image forming apparatus 100 based on a magnitude relationship between a difference value of each pixel constituting the difference image generated by the difference image generator 255 and a threshold value for concentration inspection. For example, a portion (pixel group) having a large difference value or a portion (pixel group) having a large area with a difference is a concentration defect.

Then, the inspector 259 stores an inspection result such as the position of the gloss defect or the position or type of the concentration defect, the concentration image, the glossiness image, and the difference image in the HDD 918 in association with each other, or transmits (feedbacks) these to the image forming apparatus 100.

As described above, according to the present embodiment, the degree of parallelism of the illumination light 221a emitted from the lighting device for gloss 211 can be adjusted. Therefore, irrespective of the degree of flatness of an object, a sufficient amount of regularly reflected light from the object is caused to be incident on a target area. As a result, irrespective of the degree of flatness of an object, a glossiness image is generated, which accurately reflects glossiness of the object, such that a gloss defect can be inspected (detected) with high accuracy.

In addition, according to the present embodiment, unlike a conventional lighting device, illumination light emitted from each LED is not reflected by a printed matter while an arrangement relationship of the LEDs is maintained. This prevents a joint of the LEDs from appearing in a glossiness image as a shadow and improves quality of the glossiness image.

Furthermore, according to the present embodiment, a special curved mirror as in the conventional lighting device is unnecessary. Therefore, the size and cost of the lighting device for gloss 211 can also be reduced.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

For example, in the above embodiment, the case where the lighting device for gloss 211 is used for inspection of a printed matter has been exemplified. However, an inspection target is not limited thereto, and the lighting device for gloss 211 can be also used for any inspection object in which inspection by gloss is useful. Other applications of the inspection apparatus include, but not limited to, inspection of a surface of a metal, inspection of a surface of a clear film, inspection of a surface of an injection-molded product, inspection of a surface of a resin relief printing plate, and inspection of a defect in a silicon layer of release coated paper.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

The invention claimed is:

1. A lighting device comprising:
a light emitting device including a plurality of light emitting elements arranged in curve having a first curvature; and
a honeycomb member having an extendable and contractible honeycomb structure, arranged in curve having a second curvature larger than the first curvature, in an emission direction of light emitted from the light emitting device.

2. The lighting device according to claim 1,
wherein the honeycomb member is extendable and contractible at least in a longitudinal direction of the honeycomb member, the longitudinal direction being a direction in which the plurality of light emitting elements is arranged.

3. The lighting device according to claim 2,
wherein the light emitting device and the honeycomb member are curved in the longitudinal direction about a common center of curvature.

4. The lighting device according to claim 2, further comprising:
one or more light shielding members, each configured to shield at least a part of light which has been emitted from the light emitting device and has passed through the honeycomb member in the longitudinal direction of the honeycomb member.

5. The lighting device according to claim 4, wherein the one or more light shielding members include:
a first light shielding member configured to shield light transmitted through an upper side in a lateral direction of the honeycomb member that is orthogonal to the longitudinal direction, in the longitudinal direction of the honeycomb member; and
a second light shielding member configured to shield light that has passed through a lower side in the lateral direction of the honeycomb member, in the longitudinal direction of the honeycomb member.

6. A reading device comprising:
the lighting device according to claim 1, the lighting device being configured to emit the light to an inspection object; and
an image sensor configured to detect a light level of a regularly reflected light that is reflected from the inspection object, the light level to be used for inspecting gloss of the inspection object.

7. An inspection apparatus comprising:
the reading device according to claim 6; and
a controller configured to control the reading device.

8. An inspection system comprising:
an image forming apparatus configured to form an image on a recording material; and
the inspection apparatus according to claim 7, wherein the inspection object is the recorded material having the image formed thereon.

* * * * *